Figure 1:
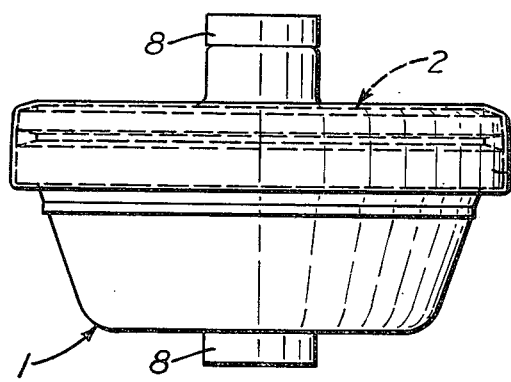

United States Patent [19]
Nebash

[11] 3,957,469
[45] May 18, 1976

[54] FILTER CASSETTE WITH REMOVABLE CAPSULE

[75] Inventor: Stanley P. Nebash, Pittsburgh, Pa.

[73] Assignee: Mine Safety Appliances Company, Pittsburgh, Pa.

[22] Filed: Feb. 3, 1975

[21] Appl. No.: 546,439

[52] U.S. Cl.................................. 55/270; 55/482; 55/501; 55/503; 73/28; 73/421.5 R; 55/320
[51] Int. Cl.² ........................................ B01D 53/30
[58] Field of Search ............ 55/270, 410, 485, 486, 55/487, 490, 494, 495, 501, 502, 503, 504, 505, 509, 510, 511, 482, 320; 73/28, 421.5 A, 421.5 R, 432 PS; 210/445, 446

[56] References Cited
UNITED STATES PATENTS

| 1,020,782 | 3/1912 | Tinker | 55/503 |
| 3,350,979 | 11/1967 | Detweiler | 55/270 X |
| 3,686,835 | 8/1972 | Strange et al. | 55/270 X |
| 3,693,410 | 9/1972 | Robrecht et al. | 55/510 X |
| 3,693,457 | 9/1972 | Pilat | 55/270 X |
| 3,782,083 | 1/1974 | Rosenberg | 55/501 X |

OTHER PUBLICATIONS

Tomb, Thomas F.; Treaftis, Harry N., A New Two-Stage Respirable Dust Sampler, American Industrial Hygenic Journal, Vol. 36, No. 1, Jan. 1975, pp. 1–9.

*Primary Examiner*—Frank W. Lutter
*Assistant Examiner*—David L. Lacey
*Attorney, Agent, or Firm*—Brown, Murray, Flick & Peckham

[57] ABSTRACT

A shallow cup has a central inlet opening in its base and a filter disc closing its open end, whereby a hollow capsule is formed. A barrier member inside the cup is located between its base and the filter and has a central portion spaced from the filter and the cup inlet. This central portion is provided with holes around a solid central area that has a diameter at least as great as the inlet opening. A separable two-part cassette contains the capsule with its marginal area clamped between the two parts. The part containing the cup is provided with a central inlet port in an end wall spaced from the capsule, and the other part of the cassette covers the filter and is provided with an outlet port. Between the capsule and inlet port in the cassette there is a baffle that causes nonrespirable particles in the incoming air to be trapped before they can reach the capsule. After a period of filtering, the cassette is opened and the preweighed capsule is removed and weighed again to ascertain the amount of particulate matter captured by the capsule.

10 Claims, 3 Drawing Figures

U.S. Patent  May 18, 1976  3,957,469

FILTER CASSETTE WITH REMOVABLE CAPSULE

In U.S. Pat. No. 3,686,835 a filter cassette is shown that contains a removable capsule, one wall of which is formed by a filter. This device is for the measurement of airborne dust, in particular respirable dust that can reach the lower part of the lungs and remain there. Respirable dust particles usually are below 5 micron size. Larger particles are usually considered nonrespirable and of no material hygenic significance. The cassette shown in the patent is used with a sampling kit having a battery powered pump and a cyclone separator. The pump draws dust-laden air through the cyclone and cassette in succession. The larger dust particles are separated from the air in the cyclone, while the respirable particles are trapped in the capsule inside the cassette. The capsule is carefully weighed before it is placed in the cassette and, after an appropriate sampling period, it is removed and again weighed. The difference in weights is the amount of dust trapped by the filter capsule, from which the respirable dust weight per cubic meter of air can be determined. The device shown in the patent performs its function very well, but if someone wishes to tamper with the device in order to record a lower dust concentration than actually exists, he can insert an instrument through the inlet of the capsule and scrape some of the dust away from the filter and then shake it out through the inlet, or he may tap the capsule to dislodge dirt collected on the filter.

It is among the objects of this invention to provide a filter device of the type shown in the above-mentioned patent, which can be used satisfactorily without a cyclone separator for nonrespirable dust particles, which cannot be tampered with without disclosing that fact and from which it is extremely unlikely that any collected dust can escape accidentally.

Figure 2:
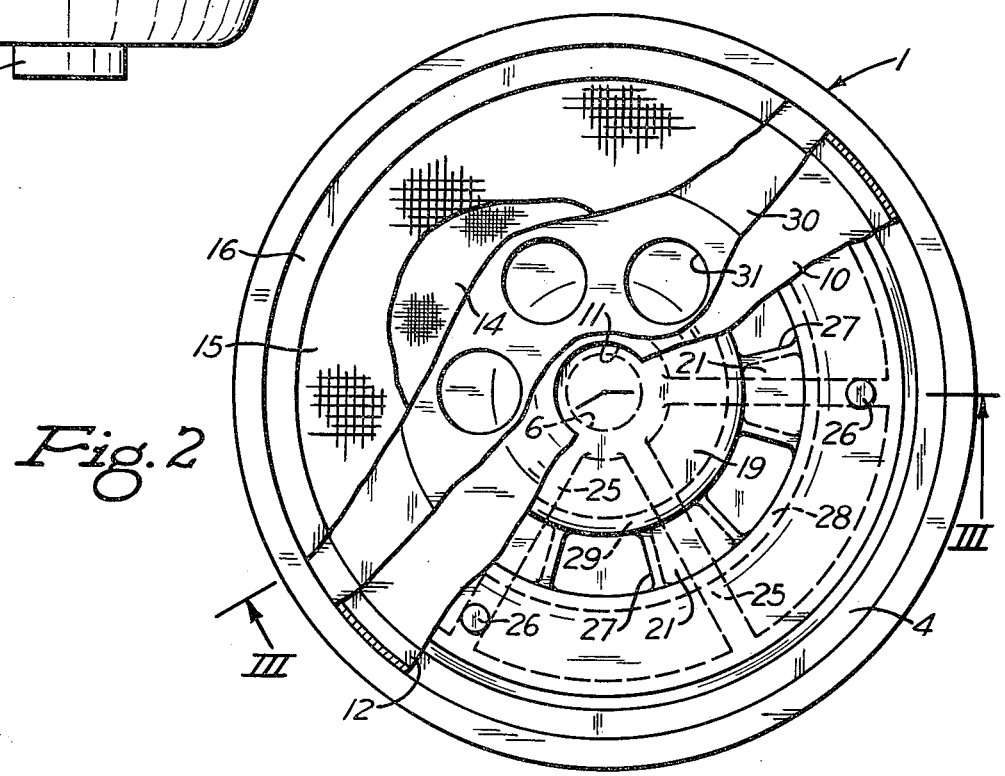
Figure 3:
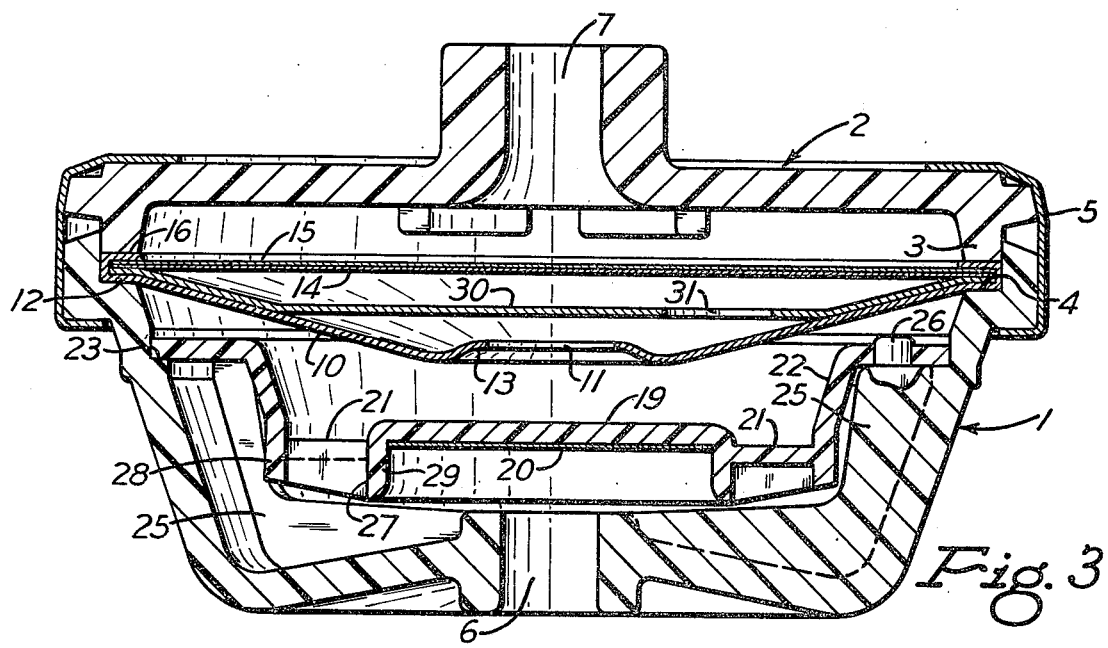

The preferred embodiment of the invention is illustrated in the accompanying drawings, in which FIG. 1 is a side view of the unit;

FIG. 2 is an enlarged plan view of the lower part of the cassette with the filter capsule broken away at different levels; and FIG. 3 is a still further enlarged cross section of the unit taken on the line III—III of FIG. 2.

Referring to FIGS. 2 and 3 of the drawings, a cassette is formed from two cup-like parts 1 and 2 that normally are sealed together but which can easily be separated. It is preferred to mold them from a plastic. One part is provided with an annular rib 3 that fits snugly enough in the other part to provide a seal, and the other part has an internal annular shoulder 4 in its open end opposing the rib. The two parts can be held together by an encircling tape 5 shrunk onto them. The tape also serves as an additional seal. However, if the tape holds the two parts of the cassette together tightly enough and forms a good enough seal in itself, it is not necessary that rib 3 form a seal with the other part of the cassette. The end wall of one part of the cassette is provided with a central inlet port 6, while the other part is provided with an outlet port 7, preferably in its end wall. By making these ports different sizes, or by providing their side walls with different outside diameters, there is no danger of becoming confused and connecting the wrong port to the pump of a dust sampling kit.

Removably disposed inside the cassette is a filter capsule that is formed from at least three elements. One of these is a shallow cup 10, preferably made of aluminum foil, but it also can be made of a high density, non-hygroscopic, stiff plastic with a very thin wall. The cup has a central inlet opening 11 in its base and an internal annular shoulder 12 in its large upper end. It is best to make the cup conical to simplify its manufacture and to reduce the material required to a minimum. The inlet is at the apex of the cup and is encircled by an inturned rim 13 that also is inclined upwardly. Overlying the cup shoulder is the edge or marginal area of the second element of the capsule, a thin filter membrane 14 in the form of a disc. If desired, in order to reinforce the filter disc and help protect it, a highly porous retaining disc 15 of the same size as the filter is placed on top of it. These two discs, or the filter disc alone if the retaining disc is omitted, are held in the cup by an inturned flange 16 integral with the open end of the cup and overlapping the margin of the retaining disc, with the edges of the two discs clamped between that flange and cup shoulder 12. The retaining disc is made of non-hygroscopic material and it is very light in weight, tough and durable. The serial number of the capsule can be printed on this disc. The flange 16 can be omitted if the edges of the two discs are cemented in place.

The capsule is placed in the cassette by inserting it in the inlet half 1 of the cassette, which preferably is the part that contains shoulder 4, and then the other half of the cassette is assembled with the first part. The rib 3 engages the flange 16 of the capsule and clamps this flange and the capsule shoulder 12 and the edges of the two discs tightly between the rib and the cassette shoulder 4, which seals against shoulder 12 to prevent dust leakage around the edge of the capsule. The shrink tape then is applied to hold the capsule together until it has been used. As shown in FIG. 1, removable plugs 8 are inserted in the inlet and outlet ports of the cassette to seal it until ready for use. These plugs can be used later, after the unit is removed from the rest of the sampling apparatus, to protect the dust sample until the capsule is removed from the cassette and weighed.

Air entering the inlet port of the cassette will pass through the capsule and leave through the outlet port 7. Dust particles in the air will be trapped inside the capsule by the filter. After a given period of time, the cassette is opened and the capsule removed from the lower half of the cassette. Dust particles which entered the capsule but did not adhere to the filter disc are supposed to remain inside the capsule, in which rim 13 around the inlet opening will help to retain them, so loss of dust during collection and subsequent handling is reduced.

When the cassette is the same shape as cup 10, as shown in the above-mentioned patent, the cassette and cup will snugly engage each other at the inner end of the cassette inlet port. In such a case, the air sample that is delivered to the cassette first flows through a cyclone separator in order to remove dust particles of nonrespirable size. On the other hand, the cyclone can be eliminated when using a cassette designed by the Bureau of Mines, in which the inlet part of the cassette is relatively deep so that the inlet end of the capsule is spaced a considerable distance from the inlet port of the cassette with a disc baffle mounted in the space between the cassette inlet and the capsule inlet. The surface of the baffle facing the cassette inlet is coated with an adhesive. The baffle blocks straight-through flow of air between the two inlets, and the adhesive traps the coarser nonrespirable dust particles that impinge against the baffle. Nevertheless, it is possible that some of the impacted dust can be dislodged from the baffle during the sampling period and be carried into the capsule, resulting in an erroneous measurement of respirable dust.

It is a feature of this invention that the cassette is provided inside with a baffle formed in such a manner that dust particles dislodged from it will not reach the filter capsule. Accordingly, the baffle has a round central impact portion 19 disposed about midway between the cassette inlet and the capsule inlet. The side of impact portion 19 facing the cassette inlet is covered with a layer 20 of tacky adhesive. This portion of the baffle blocks a straight-through flow of air between the two inlets. Radiating outwardly from the circular edge of the central impact portion of the baffle is a plurality of circumferentially spaced ribs 21 of inverted U-shape. Their outer ends are integrally connected to a circular flange 22 that extends toward the capsule and then turns outwardly to rest against a shoulder 23 formed in the side wall of the cassette. The baffle is held in this position by means of integral ribs 25 in the cassette radiating outwardly from its inlet port and having projections 26 at their outer ends extending through holes in the baffle. The exposed ends of these projections are expanded to overlap the baffle around the holes and hold it rigidly in place. Ribs 25 compartmentalize the chamber formed between the baffle and the base and side wall of the cassette. The openings 27 between ribs 21 permit the air that enters the cassette to pass the baffle and reach the inlet of the capsule. The inner and outer walls of these openings are formed by concentric flanges or walls 28 and 29 extending toward the base of the cassette.

The baffle, in addition to stopping the non-respirable dust particles before they reach the filter capsule, also prevents the capsule from being damaged by anyone inserting an object in the inlet port of the cassette. Any dust particles dislodged from the baffle and falling into the bottom of the cassette are trapped in the chamber formed beneath the baffle.

Another feature of this invention is that the capsule is less likely to have trapped particles accidentally or intentionally removed from it, which would produce a false dust concentration reading. Accordingly, a barrier member 30 is mounted inside the capsule. This barrier, like the capsule cup 10, is preferably formed from lightweight aluminum foil and is shaped like a truncated cone having a flange around it disposed between the filter disc and shoulder 12 of the capsule cup. The side wall of the barrier preferably is inclined to the same degree as the side of the capsule so that they will fit together. The central flat wall of the barrier is located about halfway between the filter 14 and the capsule inlet opening 11. The central area of this flat wall is solid and of larger diameter than inlet opening 11 of the capsule, but it is encircled by several circumferentially spaced holes 31, through which dust-laden air can flow to reach the filter. The holes in the barrier distribute the sample flow more uniformly over the filter face. Their combined area is greater than the area of the capsule inlet opening so as not to restrict the sample flow.

The purpose of barrier 30 is twofold. It prevents dust particles not adhering to or dislodged from the filter disc from falling directly out of the capsule through its inlet opening 11 and thereby reducing the sample weight. It also forms a solid barrier between the capsule inlet and the filter to prevent anyone from inserting an object through the inlet to dislodge and remove dust particles adhering to the filter. The barrier thus prevents tampering with the capsule before it is inserted in the cassette and after it is removed. At least, if it is found that the barrier is punctured or otherwise damaged, it will be evident that the sampling result probably will be erroneous.

According to the provisions of the patent statutes, I have explained the principle of my invention and have illustrated and described what I now consider to represent its best embodiment. However, I desire to have it understood that, within the scope of the appended claims, the invention may be practiced otherwise than as specifically illustrated and described.

I claim:

1. A filter unit comprising a shallow cup having a central inlet opening in its base and an annular shoulder at its open end, a filter disc in the cup having a marginal area overlying said shoulder, a barrier member disposed inside the cup between its base and the filter disc and having a central portion spaced from the disc and inlet opening, said central portion having a solid central area with a diameter at least as great as said inlet opening and coaxial with it, said central portion being provided with holes around said solid central area for passage of air, means securing the marginal areas of the disc and barrier in place so that a hollow capsule is formed that is separated into two chambers by the barrier, and a separable two-part cassette removably containing the capsule with said shoulder and marginal areas of the disc and barrier clamped between said parts, one of said cassette parts containing said cup and having an end wall provided with an inlet port, and the other of the cassette parts covering said filter disc and provided with an outlet port and having an end wall forming one wall of a chamber between said last-mentioned end wall and the capsule.

2. A filter unit according to claim 1, in which the diameter of said solid central area of the barrier is greater than the diameter of said cup inlet opening.

3. A filter unit according to claim 1, in which the open end of one of said cassette parts is provided with an internal annular shoulder and the open end of the other part of the cassette is provided with an annular rib, said cup shoulder being clamped between said cassette shoulder and rib.

4. A filter unit according to claim 1, in which said cup is provided with an inturned rim around its inlet opening.

5. A filter unit according to claim 1, in which said cup has a side wall tapered toward its inlet opening, and said barrier has a tapered side wall engaging said cup side wall.

6. A filter unit according to claim 5, in which said cup is provided with an inturned rim around its inlet opening, and the diameter of said solid central area of the barrier is greater than the diameter of said inlet opening.

7. A filter unit according to claim 1, including a baffle mounted in said one part of the cassette between its inlet port and the capsule, the baffle having a solid central impact portion spaced from said cassette inlet port and cup inlet, said impact portion having a diameter greater than said cassette inlet port and being surrounded by a flange spaced from said impact portion by ribs to form air passages through the baffle between its impact portion and flange, and the periphery of the flange engaging the surrounding side wall of the cassette.

8. A filter unit comprising a shallow cup having a central inlet opening in its base and an annular shoulder at its open end, a filter disc in the cup having a marginal area overlying said shoulder, means securing the marginal area of the disc in place so that a hollow capsule is formed, a separable two-part cassette removably containing the capsule with said shoulder clamped between said parts, one of said cassette parts containing said cup and having an end wall spaced from said capsule and provided with a central inlet port aligned with said cup inlet, and the other of the cassette parts covering said filter disc and provided with an outlet port and having an end wall forming one wall of a chamber between said last-mentioned end wall and the capsule, and a baffle mounted in said one part of the cassette containing said cup between said cassette's end wall and the capsule, the baffle having a solid central impact portion spaced from said cassette inlet port and cup inlet, said central portion having a diameter greater than said inlet port and said baffle having a peripheral flange extending toward said end wall of said one part of the cassette containing said cup to deflect incoming air toward that wall, the baffle further having a supporting flange surrounding said central portion of the baffle and spaced therefrom and connected thereto by ribs to form air passages between the central portion of said baffle and said supporting flange, said supporting flange having a portion extending from said ribs toward the capsule and spaced from the internal surface of the cassette, the portion of said supporting flange extending towards the capsule extends outwardly into engagement with the internal surface of the cassette.

9. A filter unit according to claim 8, including ribs radially positioned in said one part of the cassette containing said cup, said ribs extending outwardly into engagement with said outwardly extending portion of the supporting flange, and means connecting said outwardly extending portion of said baffle to said last-mentioned ribs.

10. A filter unit according to claim 8, in which said peripheral flange is surrounded by an annular wall extending from said supporting flange toward said end wall of said one part of the cassette containing said cup, said air passages being disposed between said peripheral flange and said annular wall.

* * * * *